United States Patent [19]

Goosen

[11] Patent Number: 5,209,726

[45] Date of Patent: May 11, 1993

[54] SELF-LUBRICATING URETHRAL CATHETER AND METHOD FOR SELF-CATHETERIZATION

[76] Inventor: Carl C. Goosen, 253 E. Webster Ave., Winter Park, Fla. 32789

[21] Appl. No.: 877,994

[22] Filed: May 4, 1992

[51] Int. Cl.[5] .............................................. A61M 25/00
[52] U.S. Cl. .................................... 604/54; 604/265; 604/280; 604/349
[58] Field of Search .............. 604/264, 265, 280, 349, 604/351, 352, 353, 49, 54, 96; 128/840, 844

[56] References Cited

U.S. PATENT DOCUMENTS

| 4,186,745 | 2/1980 | Lewis et al. ................... 604/265 |
| 5,004,455 | 4/1991 | Greenwood et al. .......... 604/280 X |
| 5,098,379 | 3/1992 | Conway et al. ................ 604/265 X |

FOREIGN PATENT DOCUMENTS

| 2616062 | 12/1988 | France ............................ 604/349 |
| 9110466 | 7/1991 | PCT Int'l Appl. ............... 604/265 |
| 1187111 | 4/1970 | United Kingdom ............. 604/280 |

Primary Examiner—Randall L. Green
Assistant Examiner—Mary Beth O. Jones
Attorney, Agent, or Firm—William M. Hobby, III

[57] ABSTRACT

A self-lubricating urethral catheter and method for self-catheterization includes a flexible sheath enclosing a perforated tube. The catheter has an insertion end and a discharge end as well as a cavity between the sheath and the tube. The cavity and conduit in the tube is filled with lubricating fluid and sealed at the discharge end. The insertion end of the catheter is inserted into a urethra. When the catheter is inserted, the sheath collapses into the tube forcing fluid in the cavity through the aperture, into the conduit and out the insertion end. This fluid being expelled lubricates the catheter as it is inserted. After the catheter is fully inserted the seal is removed from the discharge end allowing fluid and urine in the bladder to flow through the catheter.

16 Claims, 1 Drawing Sheet

SELF-LUBRICATING URETHRAL CATHETER AND METHOD FOR SELF-CATHETERIZATION

BACKGROUND OF THE INVENTION

This invention relates to catheter devices and more particularly to urethral catheters that self-lubricate when inserted into a urethra.

Patients who have no incontinence but have difficulty urinating have been trained by urologists to use catheters which are self-inserted. Self-inserting catheters enhance mobility of the patient when compared to permanent catheters as the latter is associated with recurring intransigent urinary tract and bladder infections.

The self-inserting catheters currently available for home care patients are very uncomfortable for the patient during insertion. Further, due to this uncomfortable insertion, the patients tend to empty their bladders with less than ideal frequency. Another drawback to the currently available self-inserting catheters is that these catheters tend to be reused, resulting in frequent bladder infection.

Prior to insertion the self-inserting catheters are lubricated at their tip with e.g. K-Y Lubricating Jelly. Unfortunately no matter how much lubricating jelly is applied, it is wiped off by the urethra as the catheter is advanced. For example, the distance the catheter has to traverse to enter the bladder is of the order of ten inches. After the first one or two inches, the insertion end of the catheter is essentially dry. As a result, continued advancement of the catheter is both painful and resistant to movements. Catheter designers have attempted to overcome this resistance is by increasing the stiffness of the catheter to resist kinking as it is advanced into the urethra. A catheter with increased stiffness is less flexible further adding discomfort to the patient.

SUMMARY OF THE INVENTION

This invention provides a home care patient with a relatively painless and comfortable catheter with soft flexible tubing and is self-lubricating. This self-lubricating catheter is preferably used for insertion into an urethra and includes an elongated tube enclosing a conduit containing fluid. The tube has an insertion end and a discharge end. An elongated flexible outer sheath encases the tube and has the cavity exposed between the tube and the outer sheath containing fluid. The outer sheath is operative to collapse toward the tube when inserted into the urethra. A removable sealing device engages the tube to prevent fluid from flowing through the discharge end when the outer sheath collapses. Multiple apertures are disposed between the conduit and the cavity. The apertures permit fluid to flow from the cavity through the conduit and to discharge out the insertion end to lubricate the catheter when the outer sheath collapses during insertion. This discharge of lubricant out of the insertion end lubricates the urethra while the catheter advances to the bladder.

In another aspect of the invention a method of inserting the catheter into a urethra is provided. The method includes the steps of providing an elongated tube that encloses a conduit and has an insertion end and a discharge end. The tube is encased with an elongated flexible outer sheath to form a cavity between the tube and the outer sheath. The conduit and preferably the cavity are substantially filled with fluid. Multiple apertures are provided between the conduit and the cavity. The insertion end of the elongated tube is inserted into the urethra causing the outer sheath to collapse toward the tube. In response to the collapsing outer sheath, fluid flows from the cavity through the operation to increase the pressure in the conduit. A sealing device engages the discharge end. This sealing device prevents fluid from being discharged through the discharge end when the pressure increases. In response to this pressure increase fluid passes through the conduit and out the insertion end to lubricate the catheter. Once the catheter is inserted into the bladder, the sealing device is disengaged to permit fluid and urine to pass through the conduit and out the discharge end to empty the bladder.

DESCRIPTION OF THE PREFERRED EMBODIMENTS

Figure 1:
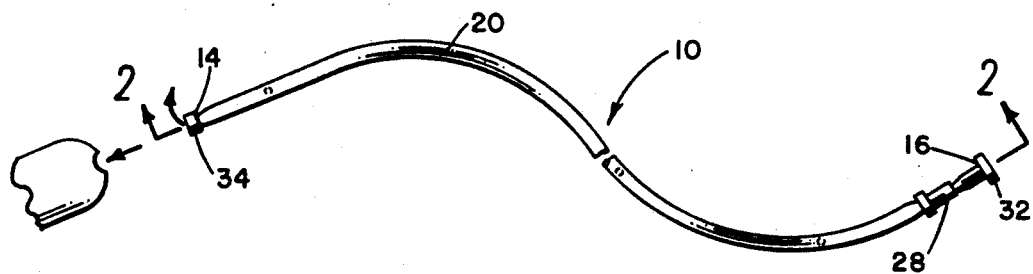
FIG. 1 is a plan view of a urethral catheter constructed according to the invention.
Figure 2:
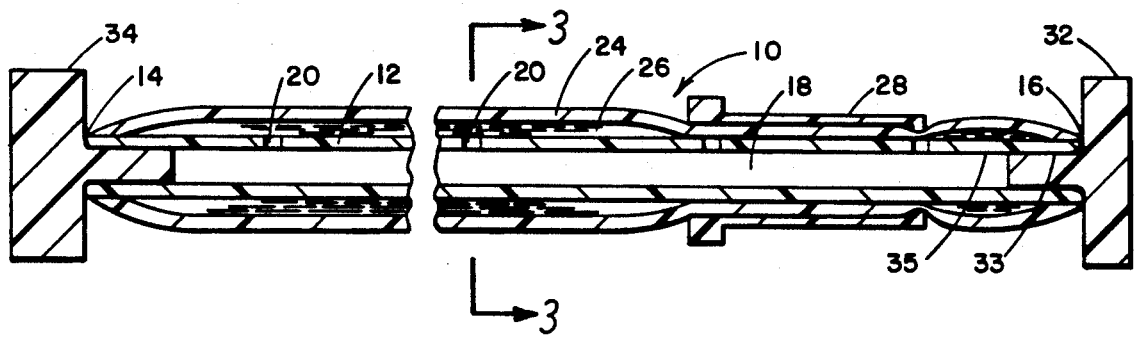
FIG. 2 is an enlarged longitudinal cross-section view of the catheter taken along line 2—2 of FIG. 1.

Referring to FIGS. 1 and 2, there is shown a new and improved catheter 10 constructed according to the invention. Preferably catheter 10 is fifteen inches long so that the catheter can be inserted into the urethra to enter the bladder. Although the invention shown is a temporary catheter for removal of urine, this invention may be equally applicable wherever a catheter is used and can be applied to temporary and to permanent style catheters.

Figure 3:
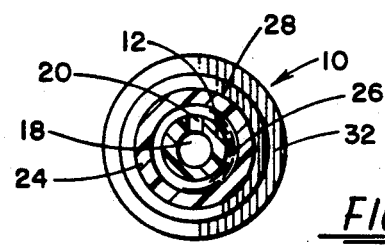
FIG. 3 is an enlarged transverse cross-sectional view taken along 3—3 of FIG. 2.

Referring to FIG. 2, generally catheter 10 includes an elongated inner tube 12 having an insertion end 14 and a discharge end 16. Referring to FIGS. 2 and 3, tube 12 encases a conduit 18 extending the length of the tube. Tube 12 has a plurality of perforations 20, also referred to as apertures, which are substantially equally spaced along the walls of tube 12 along its length.

Encasing tube 12 is an elongated flexible outer sheath 24 which also extends from the insertion end 14 to the discharge end 16. Cavity 26 is disposed between the elongated flexible outer sheath 24 and the inner tube 12. Cavity 26 is generally referred to as an annular lubricant reservoir. Sheath 24 is heat bonded at each of its ends to the discharge and insertion end of tube 12 to form a smooth taper bond. Preferably tube 12 and sheath 24 are constructed of low-durometer polyvinyl tubing.

The discharge end of tube 12 and outer sheath 24 are inserted through grip ring 28. Grip ring 28 is preferably made from a rigid plastic material and extends completely around sheath 24 adjacent to discharge end 16 of catheter 10. Grip ring 28 adjacent one end has a main portion 29 with an inner diameter "A" and a flange portion 31 at the other end with a smaller inner diameter "B". Grip ring 28 collapses a portion of sheath 24 into tube 12 when in place. Specifically, Diameter A permits "loose" fit of main portion 29 around assembly to facilitate sliding of ring 28 during assembly. Flange portion 31 has a smaller diameter B than diameter A to fit tightly on collar 10 to form a decompression groove 33 adjacent discharge end 16. Groove 33 provides stability to prevent sliding of grip ring 28 when plug 32 is being removed.

A sealing device such as a rear plug 32 is inserted into the discharge end of catheter 10. An outer plug portion 33 of rear plug 32 frictionally engages with the inner surface 35 of tube 12.

At the insertion end 14 of catheter 10, a front plug 34 is inserted through insertion end 14 and into conduit 18. Preferably front plug 34 is constructed from a rigid plastic material. When front plug 34 is inserted into insertion end 14, a fluid tight seal is formed.

Catheter 10 is loaded with fluid by introducing a mixture of preferably K-Y jelly diluted with water, through the discharge end 16 and conduit 18 until it emerges at insertion end 14. Once the conduit 18 is completely filled with fluid, plug 34 is inserted into insertion end. More lubricant is then pushed through discharge end 16 and injected into catheter 10. The fluid then passes through perforations 20 into cavity 26 between inner tube 12 and outer sheath 24. Preferably a filling syringe is used to push fluid into catheter 10 and pull out air of catheter 10 until all the air is evacuated from cavity 26. When conduit 10 is completely filled with fluid and plug 32 is inserted, the pressure in cavity 26 and conduit 18 is greater than atmospheric pressure.

Figure 4:
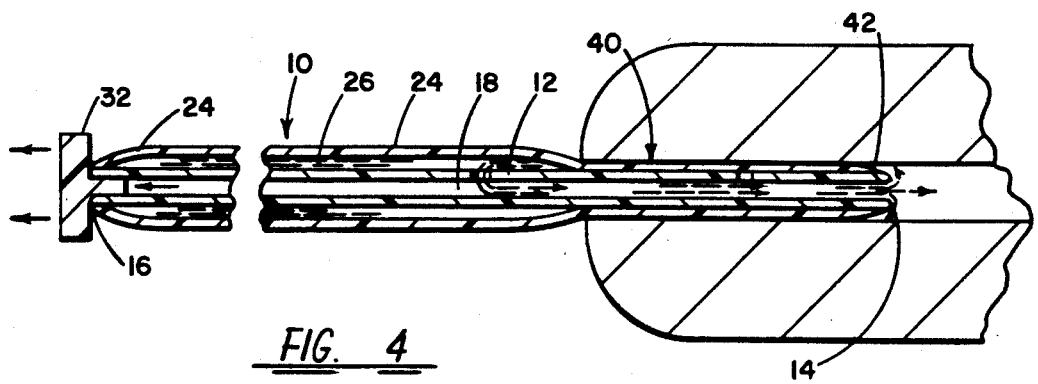
FIG. 4 is a plan view of the catheter being inserted into a urethra illustrating the self-lubricating feature according to the invention.

Referring to FIGS. 1 and 4, during operation catheter 10 is compressed between the thumb and forefinger of the person inserting the catheter adjacent insertion end 14. The front plug 34 is then removed while the tip of insertion end 14 is positioned for insertion. When plug 34 is removed, the increased pressure in conduit 10 forces lubricant to be discharged out the insertion end 14 to lubricate the ends of catheter 10.

Referring to FIG. 1, catheter 10 is then pushed into the urethra 40. The discharged lubricant lubricates the outside surface 42 of sheath 24 insertion end 14 as well as the inner surface of urethra 40.

When the elongated flexible outer sheath 24 collapses, the volume of cavity 26 decreases forcing fluid through perforations 20 into conduit 18. The pressured in conduit 18 increases in response to this collapsation.

As the rear plug 32 engages discharge end 16, the fluid is discharged out insertion end 14 and into the urethra. While the catheter continues to be advanced along urethra 40 toward the bladder, the discharged fluid lubricates the walls of the urethra so as to reduce resistance. It is recognized that as catheter 10 continues to be advanced in the urethra 40 a slight pressure builds up in cavity 26 immediately behind the area that is inserted into the urethra so as to stiffen catheter 10. The increase in stiffness prevents sheath 24 from kinking which further aids in the advancement of the catheter 10.

Once catheter 10 insertion end 14 has been fully advanced into the bladder of the patient, the rear plug 32 at distal end 16 is removed. Subsequently urine within the bladder as well as fluid within conduit 18 flows down from insertion end 14 through conduit 18 and out discharge end 16. It is recognized by the inventor that after fluid is removed from cavity 26, sheath 26 softens for comfortable removal of catheter 10. Urine passes through conduit 18 until the bladder is completely emptied. When the bladder is emptied, grip ring 28 is then grabbed by the patient and easily removed from the urethra. Since all fluid is discharged from the removed catheter 10, catheter 10 cannot be reused by the patient thereby preventing infection.

This concludes the description of the preferred embodiments. A reading by those skilled in the art will bring to mind various changes without departing from the spirit and scope of the invention. It is intended, however, that the invention only be limited by the following appended claims.

What is claimed is:

1. A self-lubricating catheter for insertion into a urethra comprising:
    an elongated tube defining a conduit, said tube containing a fluid, said tube having an insertion end and a discharge end;
    an elongated flexible outer sheath at least partially covering said tube and having a cavity disposed between said tube and said outer sheath said cavity also containing said fluid, and said outer sheath operative to collapse toward said tube when the insertion end is inserted into the urethra;
    a removable plug engaging its discharge end of said tube to prevent said fluid from flowing through said discharge end when the outer sheath collapses;
    a removable plug engaging the insertion end of said tube and
    at least one aperture disposed between said conduit and said cavity, said aperture permitting said fluid to flow from the cavity through said conduit and out said insertion end upon removal of said plug engaging said insertion end to lubricate the catheter when said outer sheath collapses during insertion.

2. The catheter as recited in claim 1 wherein said elongated tube is completely encased by the sheath and is welded to said sheath adjacent said insertion end to form a smooth tapered bond.

3. The catheter as recited in claim 1 wherein said at least one aperture comprises a plurality of apertures in walls of the tube between said insertion end and said discharge end.

4. The catheter as recited in claim 3 wherein said apertures are spaced at substantially even intervals in walls of the tube between said insertion end and said discharge end.

5. The catheter as recited in claim 1 wherein said tube and said sheath are constructed from a low-durometer polyvinyl material.

6. The catheter as recited in claim 1 wherein said fluid is a dilute solution of K-Y Jelly and water.

7. The catheter as recited in claim 1 wherein said fluid completely fills the cavity and the conduit.

8. A method of inserting a catheter into a urethra, comprising the steps of:
    providing an elongated tube that defines a conduit and has an insertion end and a discharge end;
    providing an elongated flexible outer sheath;
    forming a cavity between said tube and said outer sheath;
    providing at least one aperture between said conduit and said cavity;
    substantially filling the conduit with fluid;
    inserting the insertion end of the elongated tube into the urethra of a patient;
    collapsing the outer sheath toward said tube with the patient's urethra when the insertion end enters into the patient's urethra;
    increasing pressure in the conduit when the outer sheath collapses during insertion;

engaging said tube with a sealing device to prevent said fluid from flowing through said discharge end when the pressure in the conduit increases; and passing said fluid through said conduit and out said insertion end to lubricate the catheter when the pressure in the conduit increases.

9. The method as recited in claim 8 further comprising the steps of inserting the catheter into the patient's urethra until the insertion end passes into the patient's bladder; and collapsing the sheath into the tube to force said fluid out of the insertion end as the catheter continues to be inserted into the patient's urethra.

10. The method as recited in claim 9 further comprising the steps of disengaging the plug from the discharge end of said tube after the insertion end passes into the patient's bladder; and passing the fluid and urine through the conduit of the patient's bladder inserted catheter and out the discharge end to empty the patient's bladder.

11. The method as recited in claim 8 further comprising the steps of filling the cavity with said fluid; and passing said fluid in the cavity through the aperture and into the conduit when the sheath collapses on the inner tube.

12. The method as related in claim 8 further comprising the step of encircling the tube with the sheath.

13. A method of constructing a self-lubricating catheter comprising the steps of:

providing an elongated tube that defines an air filled conduit and has an insertion end and a discharge end;

providing a plurality of perforations along said tube between said insertion end and said discharge end;

encasing said tube with an elongated flexible outer sheath to form a cavity containing air between said tube and said outer sheath;

bonding one end of the outer sheath to the tube adjacent the insertion end;

substantially filling the conduit with said fluid from one end of the tube until the fluid emerges at the other end of the tube:

placing a plug into the insertion end of the catheter after the fluid emerges;

injecting said fluid through the discharge end of the plugged catheter and the aperture until said fluid substantially fills the cavity between the tube and the sheath and air is purged; and sealing the discharge end of the tube and sheath to prevent said fluid in the filled cavity and conduit from leaking.

14. The method as recited in claim 13 further comprising the step of sealing the discharge end by placing a grip ring over the sheath and tube; and inserting a plug into conduit through the discharge end that frictionally engages with the tube.

15. The method as recited in claim 13 further comprising the step of preparing the fluid by diluting K-Y Jelly and water.

16. The method as recited in claim 14 further comprising the steps of forming a flange portion with an inner diameter at one end of grip ring and a main portion with an inner diameter on the other end of grip ring; maintaining the inner diameter of flange portion smaller than the inner diameter of the main portion; and forming a decompression groove on the sheath with the flange portion of the grip ring.

* * * * *